United States Patent [19]

Yezrielev et al.

[11] Patent Number: 5,334,671

[45] Date of Patent: Aug. 2, 1994

[54] PHENOL TERMINATED DIESTER COMPOSITIONS DERIVED FROM DICARBOXYLIC ACIDS, POLYESTER POLYMERS OR ALKYD POLYMERS, AND CURABLE COMPOSITIONS CONTAINING SAME

[75] Inventors: Albert I. Yezrielev, Seabrook, Tex.; William E. Wellman, Edison, N.J.; Ralph M. Kowalik, Kingwood, Tex.; George A. Knudsen, Scotch Plains, N.J.; Michael G. Romanelli, Brooklyn, N.Y.

[73] Assignee: Exxon Chemical Patents Inc., Linden, N.J.

[21] Appl. No.: 6,004

[22] Filed: Jan. 15, 1993

Related U.S. Application Data

[62] Division of Ser. No. 572,754, Aug. 24, 1990, Pat. No. 5,210,155.

[51] Int. Cl.$^5$ .................... C08L 61/20; C08L 61/28; C08L 67/02
[52] U.S. Cl. .................... 525/443; 525/441; 525/442; 525/519
[58] Field of Search ............... 525/442, 443, 441, 519

[56] References Cited

U.S. PATENT DOCUMENTS

| | | | |
|---|---|---|---|
| Re. 30,102 | 9/1979 | Thomas et al. | 525/437 |
| 3,770,698 | 11/1973 | Riew | 260/47 |
| 3,787,520 | 1/1974 | Labana et al. | 260/836 |
| 3,922,447 | 11/1975 | Isaksen et al. | 428/474 |
| 3,966,837 | 6/1976 | Riew | 260/837 |
| 4,028,111 | 6/1977 | Iwasaki et al. | 96/75 |
| 4,085,086 | 4/1978 | Mizuno et al. | 260/40 TN |
| 4,101,496 | 7/1978 | Dörffel et al. | 260/31.2 R |
| 4,124,566 | 11/1978 | Saiki et al. | 528/177 |
| 4,170,580 | 10/1979 | Doerffel et al. | 260/29.4 R |
| 4,216,298 | 8/1980 | Schreckenberg et al. | 525/437 |
| 4,281,101 | 7/1981 | Schreckenberg et al. | 528/196 |
| 4,297,455 | 10/1981 | Lindner et al. | 525/439 |
| 4,507,462 | 3/1985 | Stille | 528/125 |
| 4,610,825 | 9/1986 | Rockwell | 260/410 |
| 4,927,903 | 5/1990 | Shreckenberg et al. | 528/176 |
| 5,166,289 | 11/1992 | Yezrielev et al. | 525/443 |
| 5,210,155 | 5/1993 | Yezrielev et al. | 525/442 |

FOREIGN PATENT DOCUMENTS 0287233 10/1988 European Pat. Off.

Primary Examiner—James J. Seidleck
Assistant Examiner—W. Robinson H. Clark
Attorney, Agent, or Firm—J. J. Mahon

[57] ABSTRACT

The present invention is directed towards a mixture of phenol terminated diesters and an amino crosslinking agent. The diesters are characterized by a structure consisting of

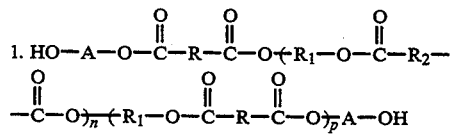

wherein R is an aliphatic divalent hydrocarbon radical containing 2 to 40 carbon atoms or a mixture of such radicals, provided however that R contains at least about 8 carbon atoms when n is 0 and p is 0, $R_1$ is an aliphatic or cycloaliphatic hydrocarbon radical containing 2 to 40 carbon atoms or a mixture of such radicals, $R_2$ is a aliphatic, aromatic or a mixture of aliphatic and aromatic hydrocarbon radicals having from 2 to 40 carbon atoms, A is divalent aromatic radical selected from the group consisting of phenylene, naphthylene or bis phenylene, p is 0 or 1, n is 0 or an integer ranging from 1 to about 40, provided however, that p is 0 when n is 0 and p is 1 when n is an integer and

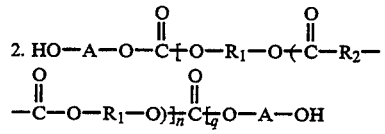

wherein q is an integer ranging from 1 to about 40, n is 0 or an integer ranging from 1 to about 40 and A, $R_1$ and $R_2$ are as defined above.

25 Claims, No Drawings

PHENOL TERMINATED DIESTER COMPOSITIONS DERIVED FROM DICARBOXYLIC ACIDS, POLYESTER POLYMERS OR ALKYD POLYMERS, AND CURABLE COMPOSITIONS CONTAINING SAME

This is a division of application Ser. No. 572,754, filed Aug. 24, 1990, now U.S. Pat. No. 5,210,155.

BACKGROUND OF THE INVENTION

This application is related to copending application Ser. No. 07/404,028, filed on Sep. 6, 1989 and is a divisional of application ser. NO. 07/572,754 which is now U.S. Pat. No. 5,210,155.

FIELD OF THE INVENTION

The present invention relates to phenol terminated diester compositions derived from dicarboxylic acid, polyester or alkyd backbone materials, to solid crosslinked polymer compositions prepared therefrom, and to methods for improving coating properties of films and surface coatings based thereon. It also relates to methods for preparing such materials containing phenolic terminal end cap groups.

DESCRIPTION OF THE RELATED ART

Coating formulations usually contain a number of components. A primary component is a resin which can be natural or synthetic- The resin acts as a polymeric coating binder or polymeric coating vehicle for the coating formulation. In addition, most coatings require a solvent, and the coating may also contain a wide variety of additives. Further, many coatings also contain a crosslinking agent, which after application of the coating vehicle to a substrate, reacts chemically with the resin during a curing stage to produce a film containing a crosslinked network. The crosslinked network is necessary for the production of good film properties. The curing stage can be conducted at ambient conditions ("air-dry system"), or at elevated temperatures ("baked system"). In either case, the solvent is evaporated during the- curing stage, resulting in a coating film. A number of properties are important for the coating film, including hardness, flexibility, weather resistance (weatherability), chemical resistance, solvent resistance, corrosion resistance, adhesion to various substrates, and impact resistance. The properties depend on may factors including type, molecular weight, monomer composition, and glass transition temperature (Tg) of the resin; type and amount of the crosslinker; curing conditions; curing catalyst; and additives, Variations of these parameters can be used to create a wide range of differences in film properties to fit requirements for a number of diverse applications. However, it is not always possible to optimize all of the desirable properties simultaneously.

For example, hardness and impact resistance are two desirable characteristics of coatings which are somewhat mutually exclusive since high hardness is usually associated with films having high Tgs and low flexibility. Conversely, high impact resistance is associated with films having low Tgs and high flexibility. This necessitates a trade-off between high hardness and high impact resistance. It is frequently possible to optimize one of these properties, but at the expense of the other.

In European Patent Application No. 0 287 233 filed Mar. 28, 1988, and published Oct. 19, 1988, Jones et al. teach a method to simultaneously obtain both high hardness and high impact resistance in a coating by employing liquid crystalline (L.C.) polymers. The L.C. polymers are characterized as containing mesogenic groups which impart the L.C. character to the polymer. The mesogenic groups are chemical structures that contain a rigid sequence of at least two, and frequently more, aromatic rings connected in the meta or para position by a covalent bond or by other rigid or semirigid chemical linkages- In addition to the mesogenic groups, the polymers contain conventional polymeric units which are attached to the mesogens via a covalent bond.

Jones formulates these L.C. polymers with suitable crosslinking resins, such as aminoplast resins, to create coating vehicles which, upon curing by baking yield films which have both high hardness and high impact values. The enhanced properties are attributed to the L.C. interaction of the various polymer chains. A mesogen which is frequently used consists of the internal esters of two or more molecules of para-hydroxybenzoic acid (PHBA). This mesogen connected to a polymeric polyol by esterification of the OH groups of the polyol with the residual carboxyl groups of the mesogen.

The L.C. polymers, while possessing good properties, have several drawbacks. First, the mesogenic groups are usually expensive to synthesize and incorporate into the polymer. For example, multiple PHBA end groups require a large quantity of PHBA and significantly increase the resin price. Second, the synthesis is complicated. In one method, the synthesis is based on the use of expensive and toxic dicyclohexylcarbodimide, which renders this method impractical from a commercial standpoint. Another method is based on direct esterification of PHBA with a polyesterdiol at 230° C. in the presence of para-toluenesulfonic acid (p-TSA). Jones teaches that it is important that an acid catalyst be used and that the temperature be controlled to provide predominantly L. C. phenolic oligoesters. Polymers produced in accordance with the teachings of Jones result, however, in material with poor color, an unacceptably high loss of PHBA via decarboxylation, and a sizable loss of phthalic acid from the polymer due to anhydride formation- In order to be commercially attractive, it would be very desirable to provide the enhanced properties associated with Jones's L.C. polymers without the above-mentioned problems.

Efforts have been made to incorporate active phenolic functionalities into polymeric coating vehicles to enhance curing characteristics or the properties of the prepared coating. However, the coatings produced in accordance with the prior art are generally inferior or difficult to prepare.

U.S. Pat. No. 4,124,566 discloses the preparation of polyester resins based on the polyester reaction product of aromatic dicarboxylic acids and diols, including hisphenols, by a two stage reaction wherein an aromatic dicarboxylic acid is first esterified by reaction with an aromatic monohydroxy compound, followed by a second stage reaction of this esterification product with a hisphenol compound or a mixture thereof with an aliphatic diol or dihydroxy benzene. These resins axe characterized as having superior thermal stability, transparency and chemical stability. Because of the high content of aromatic components, the flexibility of the resins is relatively low and the glass transition temperature is relatively high. They are also of relatively high molecular weight as evidenced by high reduced viscosities in excess of 0.9 for the materials produced.

U.S. Pat. No. 4,028,111 discloses polyester polymers based on an alternating polymer of an aliphatic dicarboxylic acid such as adipic acid and a bisphenol such as bisphenol A prepared using an excess of bisphenol such that the bisphenol groups also end-cap the polyester. The free hydroxy group of the bisphenol end cap is then reacted with a compound having quinonediazide group to produce a light sensitive polymer.

U.S. Pat. No. 4,281,101 discloses the preparation of relatively high molecular weight polycarbonates comprising reacting a mixture of an aliphatic diol, a carbonic acid bis-aryl ester such as diphenyl carbonate and a diphenyl such as bisphenol A to produce a polycarbonate polymer containing diphenyl carbonate end groups of the diphenyl compound. These polymers may then be used as a precursor for further reaction with preferably aliphatic diols and phosgene to produce thermoplastic aliphatic-aromatic polycarbonate elastomers of high molecular weight. Similar polycarbonates are disclosed in U.S. Pat. Nos. 4,216,298 and 4,297,455.

U.S. Pat. No. 3,787,520 discloses a phenolic hydroxy terminated resin which may be used as a crosslinking agent in the preparation of dry powder paint systems based on crosslinkable copolymers of glycidyl methacrylate and an ethylenically unsaturated compound. The hydroxy terminated resin is prepared by reacting an epoxy compound with a diphenol such as bisphenol A to produce a polyether terminated by the diphenol.

It is also known in the art to prepare phenol terminated liquid elastomers by reacting carboxyl terminated polymers of dienes with diphenols such as bisphenol A such that a phenolic hydroxyl group forms an end group in the polymer chain. These phenol terminated elastomers are subsequently used to cross link epoxy resins to produce an improvement in impact resistance. Examples of such systems are disclosed in U.S. Pat. Nos. 3,770,698 and 3,966,837.

U.S. Pat. No. 4,507,462 to Stille discloses biphenylene end-capped low molecular weight aromatic polymers and crosslinked versions thereof which may be prepared using a misbalanced polymerization reaction of a suitable aromatic amino ketone compound and a suitable aromatic ketomethylene compound, thereafter also adding a monofunctional biphenylene compound such as 2-acetylbiphenlene.

Various catalysts and catalyst systems have also heretofore been disclosed in the art for use in the preparation of mono- di- and polyester condensation products of organic acids and hydroxy-containing aromatic monomers. For example, U.S. Pat. No. 4,610,825 discloses the use of phosphorous acids or salts thereof as catalysts in the preparation of monoesters of a hydroxy aromatic compound such as phenol, and a carboxylic acid containing at least four carbon atoms, such as octanoic acid. Patentee indicates that the reaction product obtained is of high purity and low color.

SUMMARY OF THE INVENTION

The present invention is directed towards non-liquid crystalline phenol-terminated diester compositions which may be liquids or solids and crosslinkable formulations containing a mixture of the phenol terminated diesters and an amino crosslinking agent. These diesters are characterized by the structure of formula 1:

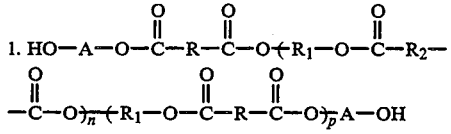

wherein R is an aliphatic divalent hydrocarbon radical containing 2 to 40 carbon atoms or a mixture of such radicals, provided however that R contains at least about 8 carbon atoms when n is 0 and p is 0, $R_1$ is an aliphatic or cycloaliphatic hydrocarbon radical containing 2 to 40 carbon atoms or a mixture of such radicals, $R_2$ is an aliphatic, aromatic or a mixture of aliphatic and aromatic hydrocarbon radicals having from 2 to 40 carbon atoms, A is divalent aromatic radical selected from the group consisting of phenylene, naphthylene or bis phenylene, p is 0 or 1, n is 0 or an integer ranging from 1 to about 40, provided however, that p is 0 when n is 0 and p is 1 when n is an integer.

Also within the scope of the present invention are crosslinkable formulations comprising a mixture of amino crosslinking agent and phenol terminated diesters based on polyester diols containing carbonate end groups or aliphatic and aliphatic/aromatic polycarbonates containing carbonate end groups characterized by the structure 2:

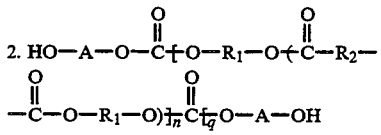

wherein q is an integer ranging from 1 to about 40, n is 0 or an integer ranging from 1 to about 40 and A, $R_1$ and $R_2$ are as defined above.

These diester oligomers or polymers are characterized by a number average molecular weight within the range of from about 500 to about 10,000.

The invention is also directed to a single stage direct esterification or multi stage esterification processes for producing the aforementioned diesters of formula 1 either with or without the use of esterification catalysts, and is particularly directed to such processes for preparing diesters of reduced color using a low temperature process in combination with catalyst systems containing a phosphorous acid or derivative thereof.

The phenol terminated diester compositions of this invention may be used as a resinous component in curable coating and paint formulations, also containing an amino crosslinking agent and other optional ingredients such as crosslinking catalyst, fillers, pigments and the like. Coatings prepared in accordance with this invention exhibit both high hardness and high impact strength, excellent weatherability, good corrosion resistance and hydrolytic stability, good solvent resistance and adhesion as well as low color and low impurity levels. These properties are produced without the incorporation of L.C. polymers or mesogenic groups into the composition, thus avoiding the many drawbacks of L.C. based polymers or polymer compositions.

DETAILED DESCRIPTION OF THE INVENTION

A first embodiment of this invention is directed towards diesters of the structure of formula 1 above and their method of preparation. These diesters may be generally categorized as the esterification product of a backbone material containing terminal carboxyl groups and a dihydric phenol such that each terminal group present on the backbone material reacts with a single hydroxy group present on the dihydric phenol resulting in an oligomer or polymer containing a free aromatic hydroxy group at terminal ends of the polymer chain. The backbone material may be composed of: (a) an aliphatic dicarboxylic acid or mixtures of such acids, having from about 8 to about 40 carbon atoms in which case n and p of formula 1 would each be 0; and (b) a carboxy-terminated polyester or polyester/alkyd reaction product of one or more aliphatic dicarboxylic acids having from 2 to 40 carbon atoms, or mixtures of such acids with one or more aromatic dicarboxylic acids having from 8 to 40 carbon atoms, in which case in formula 1, n would be an integer ranging from 1 to about 40 and p would be 1.

A second embodiment of this invention is directed towards crosslinkable coating formulations comprising a mixture of amino crosslinking agent and one or a mixture of diesters of the type (a) or (b) described above.

Yet another embodiment of the invention is directed towards crosslinkable coating formulations comprising a mixture of an amino crosslinking agent and one or a mixture of two or more diesters based on the esterification product of the aforementioned dihydric phenol and a backbone material having carbonate end groups composed of: (c) a diol or diol lengthened via carbonate linkages (—OCOO— groups) and containing terminal carbonate groups linking the diol or lengthened diol backbone to the terminal phenol end groups such as shown in formula 2 above, in which case n would be 0 and q would be equal to or greater than 1; (d) a polyester diol lengthened via carbonate linkages and containing terminal carbonate groups linking the lengthened polyester diol backbone to the terminal phenol end groups such as shown in formula 2 above in which case n would be equal to or greater than 1 and q would be greater than 1; and (e) a polyester diol containing terminal carbonate groups linking the polyester diol backbone to the terminal phenol end groups such as shown in formula 2 above in which case n would be greater than 1 and q would be equal to 1.

Diesters of type (a) described above are characterized by the following general formula 3:

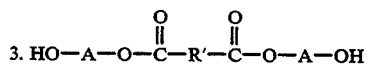

wherein R' is an aliphatic radical containing from about 8 to about 40 carbon atoms and A is as defined above.

Diesters of the type (b) described above are characterized by the following general formula 4:

wherein R is an aliphatic or cycloaliphatic radical containing from 2 to about 40 carbon atoms, n is an integer ranging from 1 to about 40, and $R_1$, $R_2$ and A are as defined above.

Diesters of type (c) above are characterized by formula 2 where n equals 0 and q is equal to or greater than 1. These materials are prepared by forming the condensation product of an aliphatic or cycloaliphatic diol having 2 to 40 carbon atoms with a diphenol such as bisphenol A and a diphenyl carbonate to form a polycarbonate having diphenyl carbonate end groups, followed by a subsequent polycondensation reaction of this precursor with a diphenol, such as bisphenol A, and phosgene to form the phenol terminated diesters. These materials are disclosed in U.S. Pat. No. 4,281,101, the disclosure of which patent is incorporated herein by reference.

Diesters of type (d) above are characterized by formula 2 where n is equal to or greater than 1 and q is greater than 1. These materials are prepared by forming the condensation product of a polyester diol and a carbonic acid bis-aryl ester such as diphenyl carbonate to form a polyester diol which has been chain lengthened via carbonate linking groups, followed by further polycondensation with a diphenol such as bisphenol A to form the phenol terminated diesters. These materials are disclosed in U.S. Pat. 4,297,455, the disclosure of which is incorporated herein by reference.

Diesters of the type (e) above are characterized by formula 2 where n is greater than 1 and q is equal to 1. These materials are prepared by forming the condensation product of a polyester diol with a carbonic acid bis-aryl ester such as diphenyl carbonate to form the polyester-diol bis-carbonic acid ester, followed by polycondensation of this precursor with a diphenol such as bisphenol A to form the phenol terminated diesters. These materials are disclosed in U.S. Pat. No. 4,216,298, the disclosure of which is incorporated herein by reference.

The phenol terminated diester polymer compositions of this invention contain no liquid-crystalline polymers or mesogenic groups, and may be further characterized as having glass transition temperatures (Tg) as low as —40° C. for the lower viscosity polymers and up to +100° C. or more for the viscous or solid polymers. These polymers may be converted into a formulated coating by adding an amino crosslinking agent and the usual solvents, pigments, and additives such as flow modifiers and stabilizers which are employed in coating compositions. The formulated coating may be applied to a substrate in the usual manner, e.g., by brushing, spraying, roller coating, or dipping. The coated substrate is then baked to form the final film by simultaneously evaporating off the solvent followed by crosslinking. The films of the invention are characterized by improved properties such simultaneous high hardness and high impact resistance, excellent weatherability, good corrosion resistance and hydrolytic stability, good solvent resistance, low impurity levels, and good adhesion when compared with films made with similar (molecular weight, functionality, etc.) polymeric materials containing no phenol terminal groups.

The diphenols which may be connected by an ester linkage to the terminal carboxyl or carbonate groups present in the backbone material are aromatic compounds having hydroxy substituent groups attached directly to the aromatic ring and may be represented by the structure:

HO—A—OH sitions of this invention is based on a carboxy terminated polyester polymer and has the structure of formula 5:

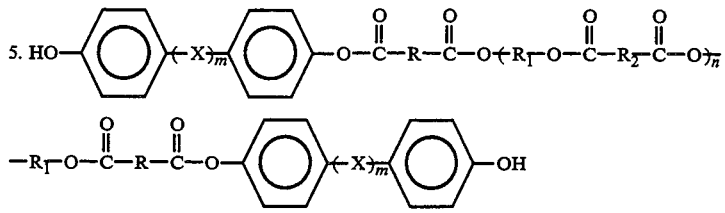

wherein A is a divalent radical selected from the group consisting of phenylene, naphthylene or bis phenylene radicals having the structure:

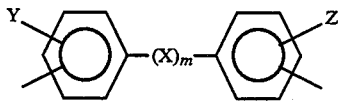

wherein m is 0 or 1, X is selected from the group consisting of a $C_1$ to $C_{12}$ hydrocarbon divalent radical, cycloaliphatic divalent radical having 5-12 carbon atoms, S, 0, and $R_4$—C—$R_4$ wherein $R_4$ may be the same or different and is selected from the group consisting of hydrogen, $C_1$ to $C_6$ alkyl, cycloalkyl, phenyl and $CF_3$, and Y and Z are independently selected from the group consisting of hydrogen, halogen, $C_1$ to $C_4$ alkyl and $C_1$ to $C_4$ alkoxy.

Examples of preferred polyhydric phenols include hydroquinone, resorcinol phenolphthalein, 1,4-dihydroxynaphthalene, 1,5-dihydroxynaphthalene, and 2,6-dihydroxynaphthalene. Examples of preferred diphenols include 2,2-bis(4-hydroxyphenyl) propane [bisphenol A], 1,1-bis(4-hydroxyphenyl) cyclohexane [bisphenol Z], 1,1-bis(4-hydroxyphenyl) ethane, (4-hydroxyphenyl) methane, 1,2-his (4-hydroxyphenyl) ethane, his (4-hydroxyphenyl) cyclohexylmethane, 3,3-bis (4-hydroxyphenyl) pentane, bis(4-hydroxyphenyl) ether, his (4-hydroxyphenyl) sulfide, and 2,2-his (4-hydroxyphenyl) hexafluoropropane.

The preferred diphenol capping agent for the purposes of this invention is hisphenol A.

The diphenols are connected to the carboxy or carbonate terminated backbone materials such that a single hydroxy group present in the diphenol reacts with a terminal aliphatic carboxyl or carbonyl group present on each end of the backbone material so that the material is capped on both ends via an ester linkage as depicted by formulas 1, 2, 3 and 4 above.

The R, $R_1$ and $R_2$ radicals may be linear or branched aliphatic or cycloaliphatic and $R_2$ may also be phenylene, naphthylene and his phenylene type aromatic radicals. These radicals may also contain internal ester groups. In the more preferred embodiment of the invention, the R, $R_1$ and $R_2$ radicals are essentially linear or branched alkenyl or alkylidene.

In the most preferred embodiment of the invention, the phenol terminated diester component of the compowherein R is a bivalent aliphatic hydrocarbon radical having from 2 to 12 carbon atoms, $R_1$ is a bivalent aliphatic hydrocarbon radical having from 2 to 12 carbon atoms, $R_2$ is the same as R or a bivalent aromatic radical having from 6 to 40 carbon atoms, including aromatic carbon atoms, m is 1, n is 1 to 40, and X is as set forth above. The more preferred range for n in this embodiment is from about 2 to about 20 and X is preferably $C(CH_3)_2$.

In the other most preferred embodiment of this invention, the phenol terminated diester component is based on a carboxy terminated dicarboxylic acid and has the structure of formula 6:

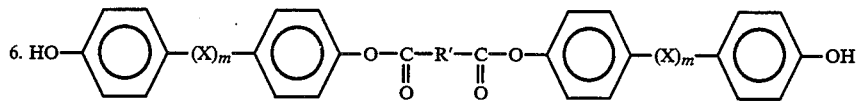

wherein R' is an aliphatic hydrocarbon radical or mixtures thereof having from 8 to 40 carbon atoms and x and m are as set forth in formula 5 above. In the most preferred embodiment, R' contains from 12 to 38 carbon atoms.

The minimum number average molecular weight for compounds of formulas 5 and 6 above which include the polymer end-capping dihydric phenols in their structure is at least about 500, more preferably at least about 1000.

The carboxy terminated polyester polymer backbone material such as depicted in formula 5 above may be formed by the condensation reaction of a diol with a molar excess of a dicarboxylic acid. The diol generally contains 2 to 20 carbon atoms and preferably contains about 2 to 10 carbon atoms, and may also contain internal ester groups. Some preferred examples of the diols are one or more of the following: neopentyl glycol; ethylene glycol; hexamethylenediol; 1,2-cyclohexanedimethanol; 1,3-cyclohexanedimethanol; 1,4-cyclohexanedimethanol; diethylene glycol; triethylene glycol; tetraethylene glycol; dipropylene glycol; polypropylene glycol; hexylene glycol; 2-methyl-2-ethyl-1,3-propanediol; 2-ethyl-1,3-hexandediol; 1,5-pentanediol; thiodiglycol; 1,3-propanediol; 1,2-propanediol; 1,2-butanediol; 1,3-butanediol; 2,3-butanediol; 1,4-butanediol; 2,2,4-trimethyl-1,3-pentanediol; 1,2-cyclohexanediol; 1,3-cyclohexanediol; 1,4-cyclohexanediol; neopentyl diol hydroxy methyl isobutyrate, and mixtures thereof.

The carboxy terminated dicarboxylic acids which may be used either in conjunction with the above referenced diols to produce the carboxyl terminated polyester polymer backbone used in preparing capped polymers of formula 5 above, or alone in producing the capped dicarboxylic acid materials of formula 6 above are dicarboxylic acids which contain from 2 to about 40 aliphatic carbon atoms or about 6 to about 40 carbon atoms, including aromatic atoms, and at least 2 carboxyl groups which may alternatively be present in the form of anhydride groups or equivalent ester forming derivatives such as the acid halide or methylester. The dicarboxylic acids are preferably one or more of the following: phthalic anhydride, terephthalic acid, isophthalic acid, adipic acid, succinic acid, glutaric acid, fumaric acid, maleic acid, cyclohexane dicarboxylic acid, azeleic acid, sebacic acid, dimer acid, pyromellitic dianhydride, substituted maleic and fumaric acids such as citraconic, chloromaleic, mesaconic, and substituted succinic acids such as aconitic and itaconic, and mixtures thereof. The most preferred acids for the purposes of this invention are linear saturated or unsaturated aliphatic dicarboxylic acids having from 2 to 10 carbon atoms such as succinic, glutaric, adipic, and similar materials. As indicated above, the carboxy-terminated dicarboxylic acids preferably contain at least about 8 carbon atoms when these materials are used alone in producing the end-capped dicarboxylic acid materials of formula 6 above.

In another embodiment, carboxy terminated oligomeric backbone material used to synthesize the diester polymers is a short chain alkyd resin. An alkyd resin is an oil modified polyester resin and broadly is the product of the reaction of a dihydric alcohol and a dicarboxylic acid or acid derivative and an oil, fat or carboxylic acid derived from such oil or fat which acts as a modifier. Such modifiers are typically drying oils. The dihydric or polyhydric alcohol employed is suitably an aliphatic alcohol. Suitable alcohols include glycol, 1,2- or 1,3-propylene glycol, butanediol, hexanediol, neopentyl glycol, and the like, Mixtures of the alcohols may also be employed. The dicarboxylic acid, or corresponding anhydrides, may be selected from a variety of aliphatic carboxylic acids or mixtures of aliphatic and aromatic dicarboxylic acids. Suitable acids and acid anhydrides include, by way of example, succinic acid, adipic acid, phthalic anhydride, isophthalic acid, and his 3,3' 4,4'-benzophenone tetracarboxylic anhydride. Mixtures of these acids and anhydrides may be employed to produce a balance of properties. As the drying oil or fatty acid there is suitably employed a saturated or unsaturated fatty acid of 12 to 22 carbon atoms or a corresponding triglyceride, that is, a corresponding fat or oil, such as those contained in animal or vegetable fats or oils. Suitable fats and oils include tall oil, castor oil, coconut oil, lard, linseed oil, palm oil, peanut oil, rapeseed oil, soybean oil and beef tallow. Such fats and oils comprise mixed triglycerides of such fatty acids as caprylic, capric, lauric, myristic, palmitic, and stearic and such unsaturated fatty acids as oleic, eracic, ricinoleic, linoleic and linolenic. Chemically, these fats and oils are usually mixtures of two or more members of the class.

These carboxyl terminated alkyd backbone polymers generally should have a number average molecular weight of from 1,000 to 3,000.

The corresponding carbonate terminated alkyds may also be used as backbone materials by forming the hydroxy terminated alkyd backbone in a manner analogous to the formation of the hydroxy terminated polyester backbone described above and using the reactants as set forth above.

As indicated above, the diestots of this invention are preferably prepared using saturated or unsaturated aliphatic diol and dicarboxylic acid starting materials. It may, however, be desirable to use some quantity of tri or tetra functional aliphatic reactants to influence viscosity and other properties of the diester material. This may be accomplished by including minor quantities, e.g. less than about 2 mole percent, of polyfunctional polyols and/or polycarboxylic acids in the esterification recipe. Examples of suitable polyols include trimethylolethane, triemthylol propane, glycerol and pentaerythritol. Examples of suitable polycarboxylic acids include trimellitic acid or anhydride.

As indicated above, the phenol terminated diesters of the present invention are particularly useful as resinous components in crosslinkable paint and coating compositions also containing an amino crosslinking agent, and other conventional additives normally present in such compositions.

The amino crosslinking agents used in the present invention are well known commercial products. They are organic compounds of the general structural type, as shown below:

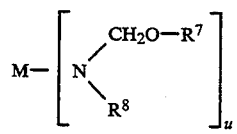

wherein
$u \geq 2$;
$R^7 =$ H, or $C_1$-$C_4$ alkyl; or $C_1$-$C_4$ alkyl
$R^8 =$ H, —$CH_2$—$OR^5$,

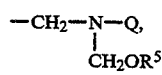

The amino crosslinking resins are produced by companies such as American Cyanamid, and Monsanto, and are made by the reaction of di(poly)amide(amine) compounds with formaldehyde and, optionally, lower alcohol.

The amino crosslinking resins that are currently produced commercially are based on:

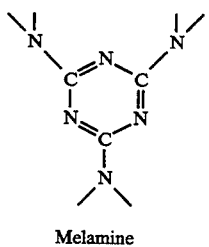

Melamine

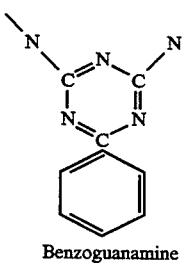

Benzoguanamine

-continued

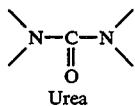
Urea

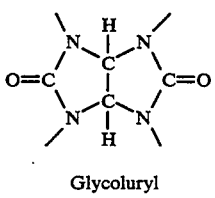
Glycoluryl

Examples of suitable amino-crosslinking resins for the diesters include:
Melamine based

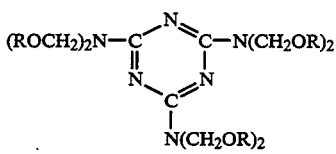

wherein
R is the following:
R=CH$_3$ (Cymel® 300, 301, 303);
R=CH$_3$, C$_2$H$_5$ (Cymel® 1116);
R=CH$_3$, C$_4$H$_9$ (Cymel® 1130, 1133);
R=C$_4$H$_9$ (Cymel® 1156); or
R=CH$_3$, H (Cymel® 370, 373, 380, 385)

The preferred melamine is hexamethoxymethylmelamine.
Benzoauanamine based resin

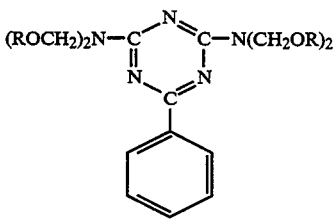

wherein R=CH$_3$, C$_2$H$_5$ (Cymel® 1123)
Urea based resins

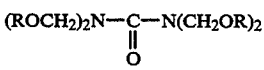

wherein
R=CH$_3$, H (Beetle 60, Beetle 65); or
R=C$_2$H$_9$ (Beetle 80).
Gycoluryl based resins

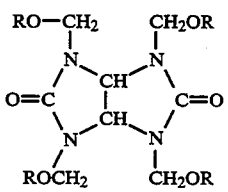

wherein:

R=CH$_3$, C$_2$H$_5$ (Cymel® 1171)
R=C$_4$H$_9$ (Cymel®1170).

In the present invention, the ratio of the active crosslinking groups, e.g., methylol (alkoxymethyl) groups of the amino crosslinking agent to the phenol groups on the phenol terminated diester is desirably from about 1.0 : 1.0 to 15.0 : 1.0, more preferably from about 1.0 : 1.0 to 5.0 : 1.0, most preferably from about 1.5 : 1.0 to 4.0 : 1.0.

On a weight basis, the amount of amino crosslinking agent effective for curing the crosslinkable binder generally ranges from about 3 to about 50 percent by weight, more preferably from about 15 to about 40 percent by weight based on the combined weight of the amino crosslinking agent, polymer and any other crosslinkable polymer constituent of the composition.

In general, quantities of crosslinking agent required to cure the composition are inversely proportional to the number average molecular weight of the ester phenol-capped polymer composition. Quantities of crosslinking agent on the higher side of this range are required to properly cure ester phenol-capped polymer compositions having a relatively low number average molecular weight, e.g., from about 500 to about 3,000, whereas lesser amounts of the crosslinking agent are required to properly cure ester phenol-capped polymers having a higher number average molecular weight, e.g., from about 3,000 up to about 10,000.

The esterification of the carboxy terminated dicarboxylic acid Dacebone or the preparation of the diphenol terminated polyester or alkyd is preferably carried out by one of several methods. In a first embodiment, a two stage reaction is used wherein a carboxy terminated polyester is formed by mixing a molar excess of aliphatic dicarboxylic acid with the appropriate diol, such as neopentyl glycol. Preferably, the molar ratio of dicarboxylic acid to diol is at least n+1:n, wherein n represents the number of moles of diol. The use of such a molar excess of acid insures that the major proportion of the resulting oligomer molecules will be terminated by acid groups. A suitable solvent and catalyst may optionally be added and the solution is stirred and heated from about 140 to 220° C. After most of the water of reaction has been removed, the diphenol is added and the second stage of the reaction is also carried out at temperatures between about 150°-260° C. The reaction can be completed by increasing the reaction temperature, preferably up to about 260° C. to esterify residual reactants.

In another embodiment, the esterification and capping reactions may be carried out in a single stage reaction. Thus, all the raw materials for forming the phenol terminated diester, including optional catalyst, may be combined and heated to a temperature of from about 140° to 220° C. Where the reactants include an aliphatic dibasic acid and aliphatic diol, these reactants will condense first because of the very high reactivity of aliphatic diols with aliphatic dibasic acids to form a carboxy terminated polyester. Then, the carboxyl functional end groups of the polyester will condense with a hydroxyl group present on the diphenol to produce the end-capped diester, during which the reaction temperatures may range from about 150°-260° C. as in the embodiment set forth above.

In another embodiment, a two stage reaction is used. In the first stage, the diphenol is mixed with a molar excess of a dicarboxylic acid such as adipic acid. Preferably, the ratio of dicarboxylic acid to the diphenol ranges from about 1 : 1 to 10: 1. A suitable solvent and catalyst may optionally be added and the solution is stirred and heated from 140°–200° C. The excess amount of acid which will be subsequently reacted helps to drive the reaction rate which allows a lower reaction temperature to be used. After most of the water of reaction has been removed, the aliphatic diol or mixture of aliphatic diols are added and the second stage of the reaction is also carried out at temperatures between 140°–200° C. This technique keeps the temperature below 200° C. The reaction can be completed by increasing the reaction temperature, preferably between about 200° and 230° C., to esterify residual reactants.

In another embodiment, the diesters based solely on an aliphatic dicarboxylic acid backbone are prepared by esterifying an aliphatic dicarboxylic acid with the diphenol at a reaction temperature below about 250° C.

The molar ratio of dihydric phenol to dicarboxylic acid and to dicarboxylic acid plus diol where carboxy terminated polyester backbone polyphers are formed, generally should be at least $2 : (n+1) : n$ respectively wherein n represents the number of moles (if any) of diol. Thus, for example, 2 moles of dihydric phenol may be reacted with one mole of dicarboxylic acid in the case where end capped acid esters are formed, and 2 moles of dihydric phenol may be reacted with 2 moles of dicarboxylic acid and one mole of diol in the case where end-capped esters of carboxy terminated polyesters are formed.

As indicated above, the diesters of this invention are free of mesogenic groups. To insure that such mesogenic groups are not formed particularly when an aromatic dicarboxylic acid is utilized as an ester-forming reactant, i.e., when $R_2$ in formula 1 above is an aromatic radical, a variation in above synthesis procedure may be employed. In one embodiment of this process variation, a three step procedure is used wherein a polyester diol is produced in the first step by forming the polyester condensation product of a molar excess of diol, such as neopentyl glycol, with a dibasic acid, which may be aliphatic, aromatic or mixtures of aliphatic and aromatic dicarboxylic acids, at a reaction temperature below about 200° C. In the second step, the resulting polyester diol is esterified with an aliphatic dicarboxylic acid, such as adipic acid, to produce a dicarboxy functional polyester. The final step is an esterification of the dicarboxy functional polymer with a diphenol, such as bisphenol-A, at a reaction temperature below about 250° C.

In a variation of the above variation, the diphenol may be first reacted with an excess of the aliphatic dicarboxylic acid at a temperature below about 200° C. to form the aliphatic half ester. This material may then be reacted with a mixture of aliphatic diol and dicarboxylic acid (aromatic, aliphatic or mixtures of aromatic and aliphatic) at a temperature below about 200° C. to form the phenol terminated diester free of mesogenic groups.

Diesters containing terminal carbonate groups linking the backbone material to the phenol may be prepared using procedures analogous to the above by condensing an aliphatic diol, a hydroxy terminated polyester or alkyd diol with diphenyl carbonate, followed by reaction with the diphenol, or by first forming the half ester of the diphenol and diphenyl carbonate followed by reaction with an aliphatic diol, hydroxy terminated polyester or hydroxy terminated alkyd. Processes for preparing these materials are disclosed in U.S. Pat. Nos. 4,281,101, 4,297,455, and 4,216,298.

It is generally known that the direct esterification of phenols by carboxylic acids does not proceed as readily as the esterification of aliphatic hydroxyl groups with carboxylic acids. In most cases when esterification of phenols is required, anhydrides or acid chlorides are used—e.g., the Schotten Baumann technique, rather than direct esterification. However, the use of anhydrides or acid chlorides for commercial production of phenyl esters is not practical because of the cost of the reagents, the highly corrosive nature of the hydrogen chloride which is formed when acid chlorides are used, as well as the substantial quantity of in by-products which must be utilized or disposed of both cases. Therefore, in order to provide a commercially acceptable process for the production of phenol terminated polymers, direct esterification of phenolic hydroxyl groups with carboxyl groups offers distinct advantages.

One method for the direct esterification of phenols was discovered by Lowrance and is disclosed in U.S. Pat. No. 3,772,389. This method uses a $H_2SO_4/H_3BO_3$ catalyst and proceeds with the high efficiency at 130°–150° C. However, the phenol terminated diester which is produced when this catalyst is used has intense color which limits application of the process.

It was surprisingly discovered that, at higher temperatures (190°–260° C.), aliphatic carboxylic groups can esterify phenols at a reasonable rate even without a catalyst. It was also found that certain combinations of compounds are particularly effective catalysts for direct esterification. They include preferably two and three valent metal compounds such as oxides, hydroxides, weak acid salts and the like, and their combinations with a strong acid such as sulfonic acid, halogen acids and the like. For metal compounds having the structure $M(OH)_n$, the ratio of equivalents of acid to equivalents of $M(OH)n$ is $<n$, preferably $<0.5$ n. A wide range of Group I to Group VI metals can be used in the reaction which include Be, Al, Cr, Mn, Fe, Co, Ni, Cu, Zn, Ga, Sn, Pb, Bi, and the like. Examples of preferred metal compounds used in the reaction are zinc acetate, calcium oxide, and sodium bicarbonate. Examples of metal compounds used in combination with strong acids are magnesium acetate methane-sulfonic acid, aluminum hydroxy acetate methane-sulfonic acid and zinc acetate-methane sulfonic acid. These catalytic systems are effective within an esterification temperature range of about 140°–200° C., preferably about 150°–190° C.

Another group of compounds effective as phenol esterification catalysts for the purposes of this invention are combinations of phosphorus based acids, such as, phosphorous or phosphoric acid with co-catalysts such as boron oxide, boric acid, and the metal (II, III) salts as defined above. Examples of such catalyst systems include $H_3PO_3$—$H_3BO_3$ and $H_3PO_3$—$ZnAc_2$. These systems catalyze phenol esterification in the temperature range of 150°–200° C.

The synthesis of phenol terminated diesters using the above mentioned systems results in products with better color than the those obtained using the $H_2SO_4/H_3BO_3$ catalyst described in U.S. Pat. No. 3,772,389.

In general, the use of high reaction temperatures for both the catalyzed and uncatalyzed reactions tends to promote color body formation. This observation can also be made with respect to the $H_2SO_4/H_3BO_3$ catalyst system described above. Catalysts which can act as oxidants or co-oxidants, such as $H_2SO_4$, are a possible cause of color body formation. Thus, the present invention additionally provides for the use of catalyst systems based on reducing acids which are known to have reducing rather than oxidizing properties. Reducing acids are acids in which the central atom is at an intermediate oxidation state. Examples of such acids are phosphorous acid, hypophosphorous acid as well as their phosphite salts and sulfinic acids such as toluene sulfinic acid, and mixtures thereof. These acids are effective as catalysts for the esterification of phenols with carboxylic acid at temperatures in the range of about 130°–190°C., preferably 140°–180° C. The synthesis of esters and particularly phenol terminated diester using these acids as catalysts results in products which have very low color. For example, a phenol terminated poller having Gardner color <1 may be obtained when hypophosphorous acid is used as a catalyst.

Where a condensation catalyst is included in the reaction mixture, it is generally used in quantities ranging from about 0.01 wt. % up to about 2.0 wt. % based on the weight of reactants.

The esterification reaction is preferably carried out in a solvent medium which is capable of dissolving at least one of the reactants. The solvent should be inert during the esterification reaction. Preferred solvents are hydrocarbons. Aromatic hydrocarbon solvents are most preferred.

The purity of phenol capped diester described above and as represented by the structure of formulas 1 and 2 above is generally not 100%. In practice the bulk of the product is as represented in formulas 1 and 2 above but also contains significant amounts of unreacted dihydric phenol as well as a diester of the dihydric phenol wherein the dihydric phenol is present as at least one recurring monomer unit in the polyester backbone chain. Generally the reaction product comprises from about 40 to 65 weight percent of phenol capped product as shown in the formulas above, the balance being a mixture of unreacted dihydric phenol and dihydric phenol diester.

The present invention also provides for a novel coating composition formed by combining the phenol terminated diesters of this invention, an amino crosslinking agent, and optionally a solvent. Application of the formulated coating can be made via conventional methods such as spraying, roller coating, dip coating, etc., and then the coated system may be cured by baking.

The same or different solvent(s) which are optionally used during the synthesis of the diester to dissolve reactants may also be added during the formulation of the coating composition to adjust viscosity so as to provide a formulation with a viscosity usually between about 10 centipoise to 10 poise. One or more solvents can be used. In many cases, a single solvent is used to solubilize the system. However, in other cases it is often desirable to use mixtures of solvents in order to effect the best solubilization, and in particular a combination of aromatic solvents with oxygenated solvents is preferred. Suitable aromatic solvents include toluene, xylene, ethylbenzene, tetralin, naphthalene, and solvents which are narrow cut aromatic solvents comprising $C_8$ to $C_{13}$ aromatics such as those marketed by Exxon Company U.S. A. under the name Aromatic 100, Aromatic 150, and Aromatic 200. The oxygenated solvents should not be extremely polar such as to become incompatible with the aromatic solvents. Suitable oxygenated solvents include propylene glycol monomethyl ether acetate, propylene glycol propyl ether acetate, ethyl ethoxypropionate, dipropylene glycol monomethyl ether acetate, propylene glycol monomethyl ether, propylene glycol monopropyl ether, dipropylene glycol monomethyl ether, diethylene glycol monobutyl ether acetate, ethylene glycol monoethyl ether acetate, ethylene glycol monobutyl ether acetate, ethylene glycol monoethyl ether, ethylene glycol monobutyl ether, diethylene glycol monoethyl ether, diethylene glycol monoethyl ether acetate, Dibasic ester (a mixture of esters of dibasic acids marketed by DuPont), ethyl acetate, n-propyl acetate, isopropyl acetate, butyl acetate, isobutyl acetate, amyl acetate, isoamyl acetate, mixtures of hexyl acetates such as those sold by Exxon Chemical Company under the brand name EXXATE ® 600, mixtures of heptyl acetates such as those sold by Exxon Chemical Company under the brand name EXXATE ® 700, acetone, methyl ethyl ketone, methyl isobutyl ketone, methyl amyl ketone, methyl isoamyl ketone, methyl heptyl ketone, isophorone, isopropanol, n-butanol, sec.-butanol, isobutanol, amyl alcohol, isoamyl alcohol, hexanols, and heptanols. The list should not be considered as limiting, but rather as examples of solvents which are useful in the present invention. The type and concentration of solvents are generally selected to obtain formulation viscosities and evaporation rates suitable for the application arid baking of the coatings. Typical solvent concentrations in the formulations range from 0 to about 75% by weight with a preferred range between about 5 and 50% by weight and a most preferred range between about 10 and 40% by weight. For the preparation of high solids coatings, the amount of solvent used in the coating formulation is preferably less than 40% of the weight of the formulation.

Satisfactory baking schedules for formulations of the present invention vary widely including, but not limited to, low temperature bakes of about 20 to 30 minutes at temperatures between 200° and 220° F. for large equipment applications and high temperature bakes of about 5 to 10 seconds in 600° to 700° F. air for coil coating applications. In general, the substrate and coating should be baked at a sufficiently high temperature for a sufficiently long time so that essentially all solvents are evaporated from the film and chemical reactions between the polymer and the crosslinking agent proceed to the desired degree of completion. The desired degree of completion also varies widely and depends on the particular combination of cured film properties required for a given application.

Required baking schedules also depend on the type and concentration of catalysts added to the formulations and on the thickness of the applied coating film. In general, thinner films and coatings with higher concentrations of catalyst cure more easily, i.e., at lower temperatures and/or shorter baking times.

Acid catalysts may be used to cure systems containing hexamethoxymethyl melamine and other amino crosslinking agents, and a variety of suitable acid catalysts are known to one skilled in the art for this purpose. These include, for example, p-toluene sulfonic acid, methane sulfonic acid, nonylbenzene sulfonic acid, dinonylnapthalene disulfonic acid, dodecylbenzene sulfonic acid, phosphoric acid, phosphorous acid, phenyl acid phosphate, butyl phosphate, butyl maleate, and the like or a compatible mixture of them. These acid catalysts may be used in their neat, unblocked form or combined with suitable blocking agents such as amines. Typical examples of unblocked catalysts are the King Industries, Inc. products with the tradename K-CURE ®. Examples of blocked catalysts are the King Industries, Inc. products with the tradename NACURE®.

The amount of catalyst employed typically varies inversely with the severity of the baking schedule. In particular, smaller concentrations of catalyst are usually required for higher baking temperatures or longer baking times. Typical catalyst concentrations for moderate baking conditions (15 to 30 minutes at 275° F.) would be about 0.3 to 0.5 wt. % catalyst solids per diester plus crosslinking agent solids. Higher concentrations of catalyst up to about 2 wt. % may be employed for cures at lower temperature or shorter times. Formulations containing sufficient residual esterification catalyst, such as phosphorous acid, may not require the inclusion of any additional crosslinking catalyst to effect a proper cure at lower curing temperatures.

In the case of formulations of this invention containing hexamethoxymethyl melamine as the crosslinking agent and p-toluene sulfonic acid as the catalyst, preferred curing conditions at dry film thickness of about 1 mil are catalyst concentration between about 0.05 and 0.6 wt. %, based on polymer solids plus crosslinking agent solids, baking temperature between 200° and 400° F. and baking time between about 5 and 60 minutes. Most preferred curing conditions are catalyst concentration between about 0.05 and 0.3 wt. %, baking temperature between about 250° and 350° F. and baking time between about 20 and 40 minutes.

As described above, the formulations of this invention are characterized by improved weather resistance. However, additional improvements in this and other properties can be achieved by including stabilizers and stabilizing systems into the formulation. Among compounds providing improvements in weather resistance are HALS (hindered amine light stabilizers), UV-screeners, antioxidants, etc. To achieve the desired color, the composition can be formulated with one or a mixture of various pigments. If pigment is added to the coating formulation, then the ratio of pigment to diester and amino crosslinking agent desirably ranges from about 0.5 : 1.0 to 5.0 : 1.0, preferably from about 0.8 : 1.0 : to 2.0 : 1.0.

Another formulating tool to improve weather resistance are silicone resins used to replace part of the diester component of the composition and impart better weather resistance to the whole system. All of these formulating approaches can be used with the diester compositions of the present invention.

The diester composition of this invention may also be blended with other crosslinkable polymer materials to improve the physical and chemical properties of the latter. Examples of suitable blend polymers include acrylic and methacrylic polymers and copolymers, epoxy resins, alkyd resins, epoxy/phenolic resins, epoxy/acrylic resins, aromatic and aliphatic urethane polymers, chlorinated rubber, nitrocellulose and other polyester resins. Respective blend ratios of 1:20 to 20:1 may be used. The diesters of this invention are particularly effective in improving the chemical resistance of alkyd resins when blended therewith at levels of from about 5 to 25% by weight.

The following examples illustrate but are not intended to limit the scope of this invention.

EXAMPLES

The following example shows the preparation of a composition containing bisphenol terminated polyester using a mixed catalyst system ($H_3BO_3/H_3PO_3$) under relatively mild esterification conditions (160°–190° C.).

EXAMPLE 1

Into a 2 liter four-necked flask equipped with a mechanical stirrer, heating mantle, nitrogen sparget, 10 inch column packed with glass beads on top of which is a Dean Stark trap and chilled water condenser, and thermometer fitted with temperature controller, are charged 228.3 g. bisphenol A (BPA), 146 g. adipic acid (AA), 52 g. neopentyl glycol (NPG), 100 g. Aromatic 100 solvent (a narrow-cut solvent of $C_8$–$C_{10}$ aromatics marketed by Exxon Company USA), 50 g. Xylene, 1.5 g. Boric acid ($H_3BO_3$), and 2.0 g. Phosphorous Acid ($H_3PO_3$). The contents are heated to melting, stirred, and heating is continued to about 160° C. where the solvent/water azeotrope starts to distill out. The solvent phase is continuously removed from the Dean Stark trap and returned to the flask. Water removal is used to monitor the reaction. The temperature is raised periodically to keep water removal at an appreciable rate. Heating is continued and the temperature allowed to rise as the water is removed to a final temperature of 190° C. The reaction is stopped after 93% of the theoretical amount of water has been removed, which takes 13.5 hours. The product is cooled and discharged. The product has an NVM (nonvolatile matter) content of 86.5%, strong acid number 1.0, carboxylic acid number 15.3, and a reduced viscosity of 0-.08 for a 10% solution in glacial acetic acid. The composition of this phenol terminated polyester can be abbreviated as follows: BPA/AA/NPG: 2/2/1.

EXAMPLES 2–5

The procedure in Example 1 is used to produce other bisphenol terminated polymers. Variations in monomer ratio, catalyst type and amount, amount of solvent, and polymerization conditions are used as shown in Table 1. Water removal is used to monitor the reaction rate and to determine the reaction time. The results are tabulated in Table 1.

EXAMPLES 6–17

The procedure of Example 1 is repeated but with other catalyst systems, solvents, and polymerization conditions, as shown in Table 2.

The following example relates to the preparation of clear films from the bisphenol terminated polyesters.

EXAMPLE 18

A clear formulation is prepared by adding the following ingredients into a clean glass jar (or metal can):

| |
|---|
| 18.2 g of bisphenol terminated polyester resin of Example 1 (86.5% nonvolatile content) |
| 5.2 g hexamethoxymethyl melamine (HMMM) as CYMEL 303 |
| 3.3 g methyl amyl ketone |
| 3.3 g methyl ethyl ketone |
| 30.0 g total |

TABLE 1

| EX. | Monomer Mole Ratio, BPA/AA/NPG | Catalyst Type, Wt. % | Wt % Solvent | Reactions Conditions | | | NVM | Reduced Viscosity |
|---|---|---|---|---|---|---|---|---|
| | | | | Time Hours | Temp Range, °C | Water Off-Take, % Theor. | | |
| 2 | 2/2/1 | 0.1% $H_3BO_3$ | 7.5% Xylene 10% Aromatic 100 | 14.5 | 160–250 | 100 | 72 | 0.07 |
| 3 | 3/2/1 | 0.64% $H_3BO_3$ 0.86% $H_3PO_3$ | 23% Aromatic 100 | 8 | 143–175 | 100 | 72 | — |
| 4 | 2/2/1 | 0.3% $H_3BO_3$ 1.0% $H_3PO_4$ | 20% Aromatic 100 | 16 | 140–200 | 84 | — | — |
| 5 | 2/2/1 | 0.6% $H_3BO_3$ 0.4% $H_3PO_4$ | 20% Aromatic 100 | 16 | 140–190 | 92 | 76 | 0.06 |

TABLE 2

| EX. | Catalyst Type | Wt. % | Solvent | Reaction Time, Hrs. | Temp. °C | Conversion % |
|---|---|---|---|---|---|---|
| 6 | $H_3BO_3$ $H_3PO_3$ | 0.15 0.20 | 10% Xylene 20% Aromatic 100 | 24 | 165–215 | 100 |
| 7 | $Al(OOC-CH_3)_2OH$ MSA* | 0.65 0.30 | 12% Heptane | 11 | 170–185 | 99 |
| 8 | $Al(OOC-CH_3)_2OH$ MSA | 0.65 0.10 | 12% Heptane | 9 | 165–190 | 99 |
| 9 | $Mg(OOC-CH_3)_2$ MSA | 0.40 0.10 | 12% Aromatic 100 | 24 | 190–230 | 81 |
| 10 | $Zn(OOC-CH_3)_2$ MSA | 0.5 0.1 | 12% Aromatic 100 | 9 | 175–190 | 100 |
| 11 | $Zn(OOC-CH_3)_2$ MSA | 0.5 0.1 | 25% Heptane | 7 | 150–190 | 100 |
| 12 | $Zn(OOC-CH_3)_2$ | 0.5 | 12% Aromatic 100 | 16 | 190–230 | 86 |
| 13 | CaO | 0.13 | 12% Aromatic 100 | 17 | 210–230 | 83 |
| 14 | $NaHCO_3$ | 0.2 | 12% Aromatic 100 | 18 | 200–230 | 88 |
| 15 | $H_3BO_3$ $H_3PO_3$ | 0.6 0.2 | 12% Aromatic 100 | 13.5 | 180–210 | 90 |
| 16 | $Zn(OOC-CH_3)_2$ $H_3PO_3$ | 0.5 0.1 | 12% Aromatic 100 | 13 | 190–210 | 86 |
| 17 | $Zn(OOC-CH_3)_2$ $H_3PO_3$ | 0.5 0.3 | 12% Aromatic 100 | 18.5 | 185–215 | 84 |

*MSA - Methane Sulfonic Acid

The container or can is then capped and sealed, placed on a roller and mixed until a homogeneous solution is obtained (about 30 minutes). After mixing, the container is allowed to stand about another 30 minutes to remove all air bubbles. The solution is then ready for application on metal test panels via drawdown rods or spray equipment.

This particular solution has the following calculated characteristics:
nonvolatile content of 70 wt. %,
Cymel 303 (HMMM) at 25 wt. % of the binder solids (polyester+HMMM)
catalyst at 0.3 wt. % $H_3PO_3$ based on binder solids (from resin synthesis)

In this formulation, the curing catalyst is the residual synthesis catalyst, and no additional curing catalyst is added. Strong acid number measurements suggest the actual catalyst level may be about one-half of the original phosphorous acid charge value of Example 1.

Formulations similar to that of Example 18 may be made using other diphenol terminated resins such as prepared in Examples 2–17. Generally speaking, the amount of crosslinking agent incorporated into the resin may range from about 15 to about 45% by weight, based on the combined weight of the resin and added crosslinking agent. The inclusion of a crosslinking catalyst may not be required where the resin contains sufficient residual esterification catalyst as in the case of Example 18. In other cases it may be necessary to include additional catalyst into the resin formulation to effect a proper cure, such cases including those where no catalyst is used in preparing the diester. Such catalysts may be typically added as dilute solutions in alcohol.

For some of the more viscous resins, the procedure of Example 18 may be altered slightly so that the diester resin and the solvent are added to the jar first. This diluted resin solution is warmed in a steam bath and then mixed on a roller until a homogeneous solution is obtained. After this solution cools to room temperature, the remaining ingredients are added and the complete formulation is again mixed on a roller to obtain a homogeneous solution.

The following example describes the preparation of cured films.

EXAMPLE 19

Thin films of the formulation of Example 18 are applied to steel test panels via drawdowns and/or air spray. The basic procedures are outlined in ASTM Test Procedure D823-87, Methods A and E. Test panels are either untreated Type QD or Type S cold rolled steel panels obtained from the Q-Panel Company or polished Bonderite 1000 (iron-phosphate treatment) panels obtained from the parker-Amchem Company. Panel sizes are either 4"×8", 3"×6", 6"×12", or 3"×5".

A model 310277 Automatic Test Panel Spray Machine made by Spraymation, Inc. is used to spray panels (Method A above); wire-wound drawdown rods and in some cases a Precision Laboratory Drawdown Machine (both from the Paul N. Gardner Company) are used to apply films via hand-pulled drawdowns (Method E). Target dry film thicknesses are 1 mil.

After wet films are applied as described above, panels are allowed to flash-off solvents for about 10 minutes at room temperature. The films are then cured by baking them in a large oven. All panels lay in a horizontal position during flash-off and baking. Backing schedules range from 10 to 60 minutes at temperatures between 220° and 350° F.

The film property evaluations which are conducted with the cured panels are as follows:

| Property/Test | ASTM Reference | Comment |
|---|---|---|
| Knoop Hardness | D1474 | — |
| Pencil Hardness | D3363 | 1 |
| Direct Impact | D2794 | 2 |
| Reverse Impact | D2794 | 2 |
| Flexibility | D1737 | 3 |
| Adhesion | D3359 | — |
| Chemical Resistances | D1308 | 4 |
| 10% HCl | | |
| 10% NaOH | | |
| Distilled H$_2$O | | |
| Methyl Ethyl Ketone | | |
| Xylene | | |
| Salt Spray (Fog) | B117 | 5 |
| Humidity | D2247 | 6 |
| Weathering | G53 | 7 |
| Permeability | D1653 | 8 |
| MEK Rubs | D3732 | 9 |

Comments
1. Gouge hardness reported (not scratch hardness).
2. ⅛ inch punch with 0.64 inch die; BONDERITE 1000 or QD panels. Values are generally higher for QD panels.
3. Cylindrical mandrel.
4. 24 hour spot tests; overall ratings: exc. > good > fair > poor; exc. means no problems other than film softening during exposure and full hardness recovery after 24 hr; poor indicates film lifted off surface or blistered; good and fair indicate some softening after recovery and/or visual gloss change (hazing); visual observations and pencil hardness measurements made at 1 and 24 hours exposure and after 24 hr. recovery with chemical removed.
5. Panels have "X" scribe (about 1.5 in. long) near bottom of panels; 0 to 10 (best ratings according to ASTM standardized scoring system for corrosion/rusting (ASTM D610) and blister size (ASTM D714); blister frequency also according to ASTM D714; reported value is for corrosion under film after 260 hr. exposure.
6. Similar scoring as for Salt Spray (comment 5 above); no scribes on these panels; reported value is again for under film corrosion but after 570 hr. exposure.
7. Accelerated weathering with Quv tester employing UVB-313 bulbs from Q-Panel Company; testing cycle 4 hr. UV at 60° C. alternating with 4 hr. moisture at 50°; reported value is 20 degree gloss loss (%) after 500 hours total exposure; glosses measured in accordance with ASTM D523; observations for checking (ASTM D660), cracking (ASTM D661), chalking (ASTM D659), corrosion (ASTM D610) and blistering (ASTM D714) also made.
8. Water vapor permeability via Method B, condition B of ASTM D1653; values reported in g/m$^2$/24 hr.
9. MEK = methyl ethyl ketone; general solvent rub method value described in paragraph 5.2 of ASTM D3732; maximum value tested is 250.

The following examples demonstrate the preparation of bisphenol terminated diesters wherein no esterification catalyst is employed.

EXAMPLES 20–24

The process of Example 1 was repeated except that the boric acid/phosphorous acid catalyst system was omitted from the reaction medium. Variations in solvents and polymerization conditions are reported in Table 3. Film properties are also reported in Table 3.

As is evident from the data in Table 3, in all cases the reaction takes place without any added catalyst. Examples 23 and 24 are similar to example 22 except the reaction time is extended to increase the conversion and lower the carboxylic acid number. A dramatic improvement in film properties results.

The following example demonstrates the use of various monomers to produce bisphenol terminated diesters.

TABLE 3

| | | | Reactions Conditions | | | Product | | Film Properties[a] | |
|---|---|---|---|---|---|---|---|---|---|
| EX. | Monomer Ratio, BPA/AA/NPG | Wt % Solvent | Time Hours | Temp °C. | Water Off-Take, % Theor. | Acid # Carboxylic | NVM | Hardness | Rev. I. |
| 20 | 2/2/1 | 10% Xylene | 12 | 180–250 | 92 | 24 | 94 | 13 | 225 |
| 21 | 2/2/1 | 8% Aromatic 150 | 10 | 180–250 | 92 | 29 | 94 | 15 | 195 |
| 22 | 2/2/1 | 8% Aromatic 150 | 7 | 180–250 | 87 | 43 | 93 | 16 | 33 |
| 23 | 2/2/1 | 8% Aromatic 150 | 10 | 170–250 | 93 | 31 | 94 | 16 | 211 |
| 24 | 2/2/1 | 8% Aromatic 150 | 13 | 180–250 | 96 | 22 | 91 | 16 | 205 |

[a]Films were prepared using 25.9% by weight Cymel 303 (based on binder; e.g. Cymel plus resin); 0.15% PTSA; and a bake schedule of 30 minutes at 300° F.

EXAMPLES 25–37

A number of bisphenol terminated diesters with different monomers were produced using a procedure similar to Example 1. The reaction conditions were:

| BPA: | 1 mole |
|---|---|
| Diacid: | 0.5–1.5 mole |
| Diol: | 0–1 mole |
| Catalyst: | 1.5 g. Boric acid |
| | 2.0 g. Phosphorous acid |
| Solvent: | 100 g. xylene |
| | 100 g. Aromatic 100 |
| Temp. Range: | 150–200° C. |
| Time: | 12–15 hours |

Clear films were made as in Examples 18 and 19 with 33% by weight Cymel 303/resin, no catalyst, and a baking schedule of 30 min. at 300° F. The results are compiled in Table 4.

Included in these examples are hisphenol terminated dicarboxylic acid materials based on a dimer acid (Example 37) and n-decanoic acid (Example 35).

The following example shows the preparation of a bisphenol terminated diester by a two-stage polycondensation technique. The advantage of the two-stage reaction is more complete incorporation of bisphenol into the polymer. The much less reactive bisphenol is reacted with diacid in the first stage under very favorable reaction conditions which include an excess of diacid and no diol present. Then the first stage product is subsequently reacted with diol in the second stage.

TABLE 4

| EX. | Type[a] | Ratio | % Conversion | Gardner Color | Strong Acid # | Carbox. Acid # | NVM | Clear Film Prop Hard | R.I. |
|---|---|---|---|---|---|---|---|---|---|
| 25 | BPA/AA/NPG | 2/2/1 | 94 | 11 | .9 | 15.1 | 89 | 8 | 66 |
| 26 | BPA/AA/NPG | 2/3/2 | 96 | 5 | .9 | 13.3 | 88 | 7 | >260 |
| 27 | BPA/SA/NPG | 2/2/1 | 92 | 8 | .7 | 23.5 | 88 | 24 | 8 |

TABLE 4-continued

| EX. | Type[a] | Ratio | % Conversion | Gardner Color | Strong Acid # | Carbox. Acid # | NVM | Clear Film Prop Hard | R.I. |
|---|---|---|---|---|---|---|---|---|---|
| 28 | BPA/SA/NPG | 2/3/2 | 96 | 3 | 1.0 | 15.2 | 91 | 20 | — |
| 29 | BPA/SA/n-$C_{10}$ | 2/2/1 | 95 | 12 | .9 | 12.1 | 75 | 11 | 60 |
| 30 | BPA/SA/CHDM | 2/2/1 | 93 | 13 | 1.0 | 16.4 | 78 | 21 | 4 |
| 31 | BPA/AA/EG | 2/2/1 | 83 | 16 | .8 | 46.2 | 85 | 20 | 32 |
| 32 | BPA/AA/EG | 2/3/2 | 89 | 14 | .8 | 36.6 | 90 | 11 | 244 |
| 33 | BPA/AA/n-$C_6$ | 2/2/1 | 94 | 16 | .7 | 16.6 | 90 | 15 | 180 |
| 34 | BPA/$C_{10}$/NPG | 2/2/1 | 98 | 5 | 1.8 | 5.0 | 89 | 2 | >260 |
| 35 | BPA/$C_{10}$/— | 2/1/0 | 98 | 16 | 1.3 | 3.8 | 83 | 17 | 200 |
| 36 | BPA/DA/NPG | 2/2/1 | 95 | 1 | .9 | 5.6 | 90 | — | — |
| 37 | BPA/DA/— | 2/1/0 | 91 | 13 | .7 | 8.6 | 80 | 1 | 165 |

[a]
SA = succinic acid
n-$C_{10}$ = 1,10 - decanediol
CHDM = Cyclohexanedimethanol
EG = Ethylene Glycol
n-$C_6$ = 1,6 - hexanediol
$C_{10}$ = n-decanedioioic acid
DA = Dimer acid; a $C_{36}$ dibasic acid produced by dimerization of a mixture of natural occurring unsaturated fatty acids, such as linoleic acid.

EXAMPLE 38

Into a 2 liter four-necked flask equipped with a mechanical stirrer, heating mantle, nitrogen sparget, 10 inch column packed with glass beads on top of which is a Dean Stark trap and chilled water condenser, and thermometer fitted with temperature controller, are charged 456.6 g. Bisphenol A, 292 g. Adipic Acid, 3.75 g. Zinc acetate, 0.76 g. Methane sulfonic acid and 200 g. Aromatic 100. The contents are heated to melting, stirred, and heating is continued to about 170° C. where the solvent/water azeotrope starts to distill out. The solvent is continuously removed from the Dean Stark trap and returned to the flask. Water removal is used to monitor the reaction. Heating is continued and the temperature allowed to rise as the water is removed to a final temperature of 180° C. The reaction is stopped after their theoretical amount of water has been removed, which takes about 4 hours. The product is then cooled to 100° C. and 104.0 g. NPG is charged to the reaction mixture. The mixture is heated at 170°–190° C. for an additional 9 hours. The water is removed as before and the total conversion is 93%. The product has an NVM=73.1% and a reduced viscosity of 0.057 for a 10% solution in glacial acetic acid. Clear films are made and evaluated as in Examples 18 and 19.

EXAMPLES 39–48

Other similar bisphenol terminated diesters are prepared as in Example 38 by simply substituting different monomers, monomer rates, solvents, catalysts, and temperature/time schedules. The results are shown in Table 5.

The following examples demonstrate the relationship of resin color on the type of catalyst employed in synthesis.

EXAMPLES 49–56

The process of Example 1 was repeated using a reaction mixture of 1.0 moles BPA, 1.0 moles AA, 0.5 moles NPG, 50 g. xylene, and 100 g. Aromatic 100 to study the effect of catalyst and reaction conditions on the color of the resin product. Gardner colors of the resin product were obtained with Gardner color standards. Clear films were prepared as in Examples 18 and 19, with a Cymel 303/resin at 33% by weight, no added cure catalyst, and a bake schedule of 10 minutes at 260° F. The results are shown in Table 6.

The following examples demonstrate that excellent combinations of film properties can be obtained for a variety of compositions and baking conditions.

EXAMPLES 57–63

A large batch of resin was produced in a manner similar to that in Example 21. Clear formulations of this large batch were then prepared with a melamine formaldehyde crosslinking agent (HMMM as CYMEL 303), a blocked PTSA catalyst (Byk Chemic VP 451) and suitable solvents. Formulation compositions contained HMMM at concentrations between 30 and 40 wt. % of binder solids and PTSA at concentrations between 0.1 and 1.5 wt. % based on binder solids.

TABLE 5

| | Monomer Ratio | Catalyst Type/ | | Stage 1 | | | Stage 2[a] | | | Product Film Props.[b] | |
|---|---|---|---|---|---|---|---|---|---|---|---|
| EX. | BPA/AA/NPG | WT % | Solvent | Time Hrs. | Temp °C. | Water Off-Take % Theor. | Time Hrs. | Temp °C. | Water Off-Take % Theor. | Carbox Acid # | Hard | R.I. |
| 39 | 2/2/1 | $H_3BO_3$/0.6 $H_3PO_3$/0.4 | 20% Aromatic 100 | 7 | 170–220 | 47.2 | 6.5 | 183–220 | 100 | 16.9 | 12.0 | 20 |
| 40 | 2/2/1 | None | 20% Aromatic 100 | 5 | 210–230 | 50 | 8 | 170–210 | 91.0 | 39.3 | 13.8 | 63 |
| 41 | 2/2/1.25 | None | 10% Aromatic 100 | 3.5 | 210–230 | 48.5 | 3 | 210–230 | 99.2 | 25.1 | 13.0 | 103 |
| 42 | 2/2/1.5 | None | 10% Aromatic 100 | 3 | 210–220 | 33 | 9 | 210–220 | 100 | 18.0 | 8.2 | 244 |
| 43 | 2/2/1 | None | 10% Aromatic 100 | 7 | 200–234 | 59 | 5 | 200–232 | 92 | 27.4 | 14.7 | 161 |
| 44 | 2/2/1 | None | 10% Aromatic 100 | 8 | 200–230 | 57.5 | 4.5 | 185–230 | 94.2 | 29.0 | 13.7 | 195 |
| 45 | 2/2/1 | None | 7.3% Toluene | 2 | 225–240 | 60 | 6 | 180–240 | 94 | 14.9 | 12.5 | 198 |
| 46 | 2/2/1 | None | 5.5% Xylene | 76 | 210–250 | 53.2 | 11 | 200–250 | 89.2 | 19.5 | 12.2 | 218 |
| 47 | 2/2/1 | None | 10.5% Aromatic 100 | 7 | 210–240 | 60.5 | 5 | 190–230 | 99.6 | 29.1 | 15.0 | 178 |

TABLE 5-continued

| EX. | Monomer Ratio BPA/AA/NPG | Catalyst Type/ WT % | Solvent | Stage 1 | | | Stage 2[a] | | | Carbox Acid # | Product Film Props.[b] | |
|---|---|---|---|---|---|---|---|---|---|---|---|---|
| | | | | Time Hrs. | Temp °C. | Water Off-Take % Theor. | Time Hrs. | Temp °C. | Water Off-Take % Theor. | | Hard | R.I. |
| 48 | 2/2/1[c] | None | 12% Aromatic 100 | 4 | 190–230 | 50 | 14 | 190–230 | 94 | — | 19.0 | 0 |

[a] Two stage esterification involved initial reaction of BPA with AA, followed by second stage reaction of theis product with NPG.
[b] Films were prepared using 25.9% Cymel 303 (based on binder; e.g. Cymel plus resin); 0.15% para Toluene Sulfonic Acid (pTSA) and a bal at 300° F.
[c] Phenolphthalein substituted for bisphenol A. Hardness was increased at expense of flexibility.

TABLE 6

| EX. | Catalyst System | Temperature Range, °C. | Reaction Time, hrs. | % Conversion | Gardner Color | Clear Film Properties | | Comments |
|---|---|---|---|---|---|---|---|---|
| | | | | | | Hard | R.I. | |
| 49 | 2.0 g. $H_3PO_3$ 1.5 g. $H_3BO_3$ | 150–204 | 10 | 94 | 14 | 4 | <10 | (1) |
| 50 | 1.6 g. $H_2SO_4$ 6.1 g. $H_3BO_3$ | 133–146 | 15 | 100 | 18 | — | — | (1) |
| 51 | 4.6 g. $H_3PO_4$ (85%) | 156–175 | 37 | 92 | 12 | — | — | (1) |
| 52 | 4.6 g. $H_3PO_4$ (85%) 4.0 g. $Ph_3P$ | 159–172 | 29 | 86 | 11 | — | — | (1) |
| 53 | 4.0 g. $(PhO)_3P$ | 160–187 | 34 | 91 | 8 | — | — | (1) |
| 54 | 4.0 g. $H_3PO_3$ | 151–173 | 14 | 94 | 3 | 17 | 140 | (2) |
| 55 | 4.0 g. $H_3PO_3$ 4.0 g. $(PhO)_3P$ | 155–170 | 13 | 96 | 2 | 18 | 180 | (2) |
| 56 | 8.1 g. $H_3PO_2$ (50%) | 142–170 | 16 | 95 | <1 | 21 | >200 | (2),(3) |

Comments:
(1) These catalyst systems gave dark colored resin solutions despite conversion levels and reaction conditions.
(2) Catalysts which are reducing agents and low reaction temperatures gave improved color and good film properties.
(3) Hypophosphorous acid catalyst gave best color.

The formulations were drawn down to approximately 1 mil dry films on cold rolled steel test panels (Q-Panel Company, type QD) and baked at temperatures between 220° and 300° F. for times between 10 and 50 minutes Cured films were evaluated for Knoop hardness, reverse impact, MEK double rubs, gloss retention after 1 hour immersion in boiling water, and resistance to 10% NaOH (24 hour spot test). Results indicate that excellent combinations of film properties can be obtained for a variety of compositions and baking conditions as shown in Table 7.

300 g $TiO_2$ (DuPont TI-PURE R-960)
20 g. Xylene
Complete Formulation:
200 g. Mill Base
9.6 g. bisphenol terminated diester resin (nonvolatile content 86.5%)
31.1 g. Cymel 303 (HMMM)
2.0 g. Byk-Chemie Product VP-451 (amine blocked p-TSA)
21.7 g. EXXATE 700 Solvent (a mixture of heptyl acetates sold by Exxon Chemical Company)
29.7 g. Xylene

TABLE 7

| EX. | HMMM WT % | Cat WT. % | Bake Temp, °F. | Bake Time, Min. | Clear Film Tests | | | | |
|---|---|---|---|---|---|---|---|---|---|
| | | | | | Knoop Hard | Reverse Impact | MEK Rubs | Gloss Retent. | NaOH Spot |
| 57 | 30 | 0.3 | 300 | 10 | 15.5 | 83 | >200 | 21.8 | no effect |
| 58 | 30 | 0.3 | 300 | 10 | 17.0 | 85 | >200 | 13.6 | no effect |
| 59 | 30 | 0.1 | 300 | 30 | 14.6 | 112 | >200 | 54.3 | no effect |
| 60 | 40 | 0.3 | 260 | 50 | 14.5 | 106 | >200 | 22.9 | no effect |
| 61 | 40 | 1.0 | 220 | 30 | 16.3 | 150 | >200 | 18.5 | no effect |
| 62 | 30 | 0.5 | 260 | 10 | 15.5 | 125 | >200 | 10.7 | no effect |
| 63 | 30 | 0.5 | 260 | 10 | 14.2 | 120 | >200 | 3.5 | discolored |

The following example describes the preparation of pigmented paints.

EXAMPLE 64

Pigmented paints are prepared by grinding titanium dioxide ($TiO_2$) into the clear formulations using a high speed disk disperser such as the Byk-Chemie DISPERMAT Model CV. First a mill base containing $TiO_2$, bisphenol terminated diester resin, and solvent is ground; then this mill base is let down with the remaining ingredients in the formulation. Specific weights for one paint are given below:
Mill Base:
300 g. of bisphenol terminated diester resin (similar to that resin described in Example 1 but NVM=86.5%)

This paint has a nonvolatile content of 75.5 wt. %, a pigment/binder weight ratio of 0.8, a HMMM concentration of 24 wt. % of binder and a catalyst level of 0.27 wt. % p-TSA based on binder.

The paint may then be applied to an appropriate substrate by drawdown or spraying, followed by baking as set forth above.

Other paints may be made with different resins; HMMM concentrations between 20 and 35 wt. % of binder; amine-blocked P-TSA, phosphoric acid catalysts; catalyst levels between 0 and 0.6 wt. % on binder; pigment/binder weight ratios between 0.8 and 1.1 and variety of solvents including mixtures of Aromatic 100, Aromatic 150, Xylene, n-BuOh, EXXATE 600 solvent, EXXATE 700 solvent, methyl amyl ketone and methyl ethyl ketone.

Commercial pigment wetting/dispersing additives may also be used in some paints. These include Byk-Chemie ANTI-TERRA U, DuPont ELVACITE AB 1015 and ICI SOLSPERSE 24000. They are used at concentrations between 1 and 2.5 wt. % active ingredient based on pigment. Dow Corning 57 flow additive may also be added to some formulations, typically at a concentration of 0.1 wt. % of the formulation.

What is claimed is:

1. A polymer composition comprising a homogeneous mixture of:

a. a non-liquid crystalline phenol terminated diester composition having a number average molecular weight within the range of about 500 to about 10,000 and having a structure selected from the group consisting of:

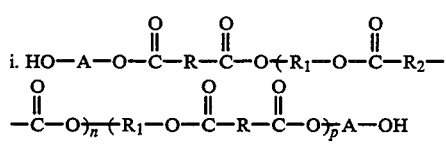

and

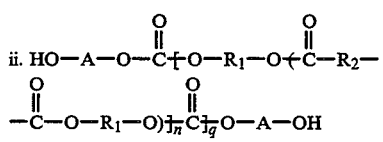

wherein R is an aliphatic divalent hydrocarbon radical containing 2 to 40 carbon atoms or a mixture of such radicals, provided however that R contains at least about 8 carbon atoms when n is 0, $R_1$ is an aliphatic or cycloaliphatic hydrocarbon radical containing 2 to 40 carbon atoms or a mixture of such radicals, $R_2$ is an aliphatic, aromatic or a mixture of aliphatic and aromatic hydrocarbon radicals having from 2 to 40 carbon atoms, A is divalent aromatic radical selected from the group consisting of phenylene, naphthylene or bis phenylene, p is 0 or 1, n is 0 or an integer ranging from 1 to about 40, provided however, that p is 0 when n is 0 and p is 1 when n is an integer, and q is an integer ranging from 1 to 40, mixed with b. an amount of an amino crosslinking agent effective for curing the phenol terminated diester composition.

2. The composition of claim 1 wherein A is a bis-phenylene radical having the structure:

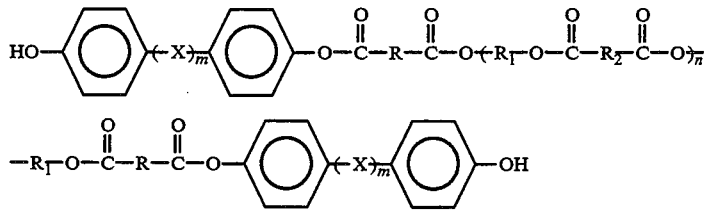

wherein m is 0 or 1, and X is selected from the group consisting of a $C_1$ to $C_{12}$ hydrocarbon divalent radical, a cycloaliphatic divalent radical having 5 to 12 carbon atoms S, O, and $$R_4-\overset{|}{\underset{|}{C}}-R_4$$

wherein $R_4$ may be the same or different and is selected from the group consisting of hydrogen, $C_1$ to $C_6$ alkyl, cycloalkyl, phenyl and $CF_3$, and Y and Z are independently selected from the group consisting of hydrogen, halogen, $C_1$ to $C_4$ alkyl and $C_1$ to $C_4$ alkoxy.

3. The composition of claim 1 wherein said phenol terminated diester has the structure:

HO—A—O—C(=O)—R—C(=O)—O(—$R_1$—O—C(=O)—$R_2$—C(=O)—O)$_n$(—$R_1$—O—C(=O)—R—C(=O)—O)$_p$A—OH

4. The composition of claim 3 wherein A is:

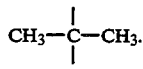

5. The composition of claim 3 wherein said phenol terminated diester has the structure:

HO—⬡(—X)$_m$⬡—O—C(=O)—R—C(=O)—O(—$R_1$—O—C(=O)—$R_2$—C(=O)—O)$_n$—$R_1$—O—C(=O)—R—C(=O)—O—⬡(—X)$_m$⬡—OH wherein n is an integer ranging from about 1 to about 40.

6. The composition of claim 5 having a number average molecular weight within the range of from about 500 to about 6000.

7. The composition of claim 5 wherein m is 1 and X is $$CH_3-\overset{|}{\underset{|}{C}}-CH_3.$$

8. The composition of claim 3 wherein n is zero, p is zero, and R is a divalent organic radical containing from 10 to 40 carbon atoms, 9. The composition of claim 5 wherein $R_1$ contains from 2 to 8 carbon atoms, 10. The composition of claim 9 wherein $R_1$ is derived from neopentyl glycol, 11. The composition of claim 9 wherein R contains from 2 to 12 carbon atoms.

12. The composition of claim 11 wherein R is derived from one or a mixture of aliphatic dicarboxylic acids.

13. The composition of claim 11 wherein m is 1 and X is

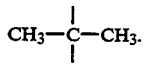

14. The composition of claim 5 wherein $R_1$ is derived from neopentyl glycol and R and $R_2$ are derived from adipic acid, and n ranges from about 2 to about 20.

15. The composition of claim 3 wherein the ratio of active crosslinking groups on the amino crosslinking agent to free phenol groups on the diester ranges from about 1.0 : 1.0 to about 15.0 : 1.0.

16. The composition of claim 3 which contains from about 3 to about 50 parts by weight of amino crosslinking agent based on the combined weight of amino crosslinking agent and crosslinkable polymer.

17. The composition of claim 15 wherein the amino crosslinking agent is derived from a melamine, a benzoquanamine, a urea or a glycoluryl.

18. The composition of claim 17 wherein the amino crosslinking agent is derived from a melamine.

19. The composition of claim 18 wherein the melamine is hexamethoxymethylmelamine.

20. The composition of claim 3 further containing an amount of solvent effective to provide a coating formulation with a viscosity between about 10 centipoise to 100 poise.

21. The composition of claim 20 wherein the amount of solvent is less than about 40 percent of the weight of the composition.

22. The composition of claim 3 further containing an amount of acid catalyst effective to initiate a crosslinking reaction upon the application of heat.

23. The composition of claim 22 wherein said acid catalyst is selected from the group consisting of alkyl or aromatic sulfonic acids and blocked alkyl or aromatic sulfonic acids.

24. The composition of claim 3 further containing one or more pigments.

25. A solid crosslinked polymer composition prepared by curing the diester composition of claim 18 or claim 15.

* * * * *